United States Patent
Lu et al.

(10) Patent No.: US 11,578,023 B2
(45) Date of Patent: Feb. 14, 2023

(54) METHOD AND CATALYST FOR PRODUCING METHYLBENZYL ALCOHOL FROM ETHANOL BY CATALYTIC CONVERSION

(71) Applicant: DALIAN UNIVERSITY OF TECHNOLOGY, Liaoning (CN)

(72) Inventors: Anhui Lu, Liaoning (CN); Wencui Li, Liaoning (CN); Qingnan Wang, Liaoning (CN)

(73) Assignee: DALIAN UNIVERSITY OF TECHNOLOGY, Dalian (CN)

( * ) Notice: Subject to any disclaimer, the term of this patent is extended or adjusted under 35 U.S.C. 154(b) by 22 days.

(21) Appl. No.: 16/973,592

(22) PCT Filed: Sep. 28, 2018

(86) PCT No.: PCT/CN2018/108268
§ 371 (c)(1),
(2) Date: Dec. 9, 2020

(87) PCT Pub. No.: WO2020/051957
PCT Pub. Date: Mar. 19, 2020

(65) Prior Publication Data
US 2021/0246092 A1 Aug. 12, 2021

(30) Foreign Application Priority Data
Sep. 10, 2018 (CN) .......................... 201811048385.3

(51) Int. Cl.
C07C 29/34 (2006.01)
C07C 29/32 (2006.01)
(Continued)

(52) U.S. Cl.
CPC ................. *C07C 29/34* (2013.01); *B01J 8/06* (2013.01); *B01J 21/066* (2013.01); *B01J 21/08* (2013.01);
(Continued)

(58) Field of Classification Search
None
See application file for complete search history.

(56) References Cited

U.S. PATENT DOCUMENTS

2015/0183694 A1* 7/2015 Blommel ................. C10G 3/42
585/322

FOREIGN PATENT DOCUMENTS

CN 104039741 A 9/2014
CN 109111344 A 1/2019

OTHER PUBLICATIONS

Supporting information of Moteki, T. et al. "Self-Terminated Cascade Reactions That Produce Methylbenzaldehydes from Ethanol" ACS Catal. 2016, 6, 11, 7278-7282, pp. 1-12 (Year: 2016).*
(Continued)

*Primary Examiner* — Medhanit W Bahta
(74) *Attorney, Agent, or Firm* — Muncy, Geissler, Olds & Lowe, P.C.

(57) ABSTRACT

The present invention relates to methods and catalysts for producing methylbenzyl alcohol from ethanol by catalytic conversion, and belongs to the field of chemical engineering and technology. The present invention develops a route of producing methylbenzyl alcohol starting from green and sustainable ethanol and provide corresponding catalysts used for the catalytic conversion route. This innovative reaction route has several advantages, such as, simple process, eco-friendly property, and easy separation of products, as compared with a traditional petroleum-based route. This present route has a reaction temperature of 150-450° C. and (Continued)

total selectivity of 72% for methylbenzyl alcohol, and has good industrial application prospect. The innovation of this patent comprises the catalysts synthesis and the reaction route.

5 Claims, 2 Drawing Sheets

(51) Int. Cl.
    *C07C 29/36*     (2006.01)
    *B01J 8/06*     (2006.01)
    *B01J 21/06*     (2006.01)
    *B01J 21/08*     (2006.01)
    *B01J 21/10*     (2006.01)
    *B01J 21/18*     (2006.01)
    *B01J 23/06*     (2006.01)
    *B01J 23/72*     (2006.01)
    *B01J 27/185*     (2006.01)
    *B01J 35/00*     (2006.01)
    *B01J 35/02*     (2006.01)
    *B01J 37/02*     (2006.01)
    *B01J 37/08*     (2006.01)
    *B01J 37/18*     (2006.01)

(52) U.S. Cl.
    CPC .............. *B01J 21/10* (2013.01); *B01J 21/18* (2013.01); *B01J 23/06* (2013.01); *B01J 23/72* (2013.01); *B01J 27/1853* (2013.01); *B01J 35/0006* (2013.01); *B01J 35/026* (2013.01); *B01J 37/0207* (2013.01); *B01J 37/0236* (2013.01); *B01J 37/082* (2013.01); *B01J 37/18* (2013.01); *C07C 29/32* (2013.01); *C07C 29/36* (2013.01); *B01J 2208/025* (2013.01)

(56) References Cited

OTHER PUBLICATIONS

Iwasa, N. et al. "Difference in the reactivity of acetaldehyde intermediates in the dehydrogenation of ethanol over supported Pd catalysts" Catalysis Letters 62 (1999) 179-184 (Year: 1999).*

Mondal, S. et al. "Low temperature wet-chemical synthesis of spherical hydroxyapatite nanoparticles and their in situ cytotoxicity study" Advances in Nano Research, vol. 4, No. 4 (2016) 295-307 (Year: 2016).*

Moteki. T. et al. "Self-Terminated Cascade Reactions that Produce Methylbenzaldehvdes 7-9 from Ethanol." *Catalysis.*, vol. 6, No. (11), Sep. 28, 2016 (Sep. 28, 2016), pp. 7281-7282.

Lu Zhang et al.; "Synthesis of C4 and C8 Chemicals from Ethanol on MgOIncorporated Faujasite Catalysts with Balanced Confinement Effects and Basicity" ChemSusChem, Mar. 3, 2016, 9, pp. 736-748.

* cited by examiner

METHOD AND CATALYST FOR PRODUCING METHYLBENZYL ALCOHOL FROM ETHANOL BY CATALYTIC CONVERSION

TECHNICAL FIELD

The present invention relates to methods and catalysts for producing methylbenzyl alcohol from ethanol by catalytic conversion, and belongs to the field of chemical engineering and technology.

BACKGROUND

Methylbenzyl alcohol with oxygen containing groups is an important organic chemical intermediate, and is produced from xylene by oxidation at high pressure (0.4-3.0 MPa). Xylene is produced by steam cracking or catalytic reforming of naphthol derived from petroleum. However, under severe oxidation conditions, the obtained target products are further oxidized to produce a large amount of derivatives of aid and ester, resulting in low selectivity (~40%) of the target products and difficulty in separation of products. However, the target products shift of the oil refinery to gasoline, causing global shortage of aromatic feedstock. Therefore, it is urgent to develop a route to produce methylbenzyl alcohols from other alternative feedstocks directly.

The availability of the ethanol is further increased on basis of the industrialization of ethanol production from syngas and through fermentation of biomass. The ethanol in China has an output of up to 15 million tons in 2015. The ethanol as an available platform molecule with oxygen groups can be converted into oxygenates such as acetaldehyde and high carbon alcohols ($C_{4-12}$) through dehydrogenation, C-C coupling and dehydrocyclization reaction. However, the currently reported catalysts show poor selectivity for high chain products, especially aromatic oxygenates, because of the co-existence of several complicated competition reactions during the ethanol chain growth process. Resasco et al. adopt acetaldehyde-ethanol mixture as the reactant and detect only a small amount of tolyl aldehyde produced on MgO and MgO modified faujasite [*ChemSusChem* 2016, 9, 736]. Flaherty et al. adopt a co-feed of acetaldehyde-ethanol mixture (acetaldehyde/ethanol=1:3) and detect tolyl aldehyde and xylyl alcohol produced on the hydroxyapatite catalyst, the selectivities are respectively 30% and 3%, and the conversion of acetaldehyde is 55% [*ACS Catal.* 2016, 6, 7278]. To sum up, it is extremely challenging to producing aromatic oxygenates from ethanol by efficient catalytic conversion.

Therefore, the development of a route for direct conversion of ethanol to methylbenzyl alcohol saves energy, achieves high efficiency, meets the urgent demand for sustainable development and then, can possibly replace or partially replace the petroleum-based routes. On the other hand, a direct production technology also contributes to alleviate aromatics shortage and ensure the safety of social and economic development in China.

SUMMARY

The purpose of the present invention is to develop a route of producing methylbenzyl alcohol starting from sustainable ethanol and provide corresponding catalysts used for the catalytic conversion route. The present invention emphasizes on low reaction temperature and a double bed catalyst reaction system.

A total reaction formula is as follows:

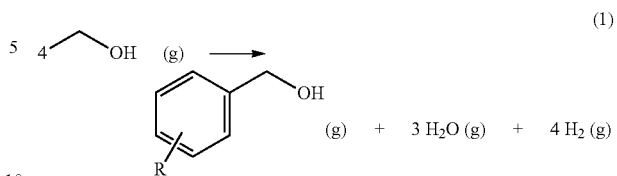

This innovative reaction route has several advantages, such as simple process, eco-friendly property, and easy separation of products, as compared with a traditional petroleum-based route. This present route has a reaction temperature of 150-450° C. and total selectivity of 72% for methylbenzyl alcohol, which is much higher than the currently reported catalyst level, and has good industrial application prospect. The innovation of the patent comprises the catalytic synthesis and the reaction route.

The technical solution of the present invention is:

A method for producing methylbenzyl alcohol from ethanol by catalytic conversion comprises the following steps:

(1) production of dehydrogenation catalyst (1.1) preparing transition metals aqueous solution and/or alcohol solution;

(1.2) using an incipient wetness impregnation method to impregnate a support for 1-3 times using the transition metals aqueous or alcohol solution prepared in the step (1.1); after impregnation, stayed at room temperature for 0.1-2 h;

(1.3) placing the obtained mixture from the step (1.2) into a 50° C. oven for drying for 0.1-20 h;

(1.4) drying the dried product in the step (1.3) at 100-150° C. for 0.5-2 h, and treating the catalyst precursor in inert and hydrogen atmosphere in sequence or in hydrogen atmosphere directly to obtain supported transition metal catalysts, i.e., dehydrogenation catalyst, recorded as transition metals/support;

transition metals are selected from one or a combination of more than one of Co, Ni, Cu, Ag, Pd, Rh, Ru, Pt, Ir, Zn and Y;

If the support is carbon or carbon/oxide compounds, the obtained catalyst precursor is treated in inert atmosphere at 350-450° C. for 1-5 h, and then reduced in hydrogen atmosphere at 350-600° C. for 0.5-5 h;

If the support is $Al_2O_3$, $SiO_2$, $ZrO_2$, ZnO or MgO, the obtained catalyst precursor is reduced directly in hydrogen atmosphere at 350-600° C. for 2-5 h;

(2) producing aromatization catalyst (2.1) dissolving the nitrates of metals A, B, C, D and E in water to prepare the corresponding aqueous solutions;

(2.2) dissolving diammonium phosphate in water to prepare the corresponding aqueous solution;

(2.3) adding the nitrate solutions prepared in the step (2.1) in the aqueous solution prepared in the step (2.2) dropwise, and fully stirring; wherein the molar ratio of metals to phosphorus is 1.5-1.67;

(2.4) using ammonia water to adjust the pH value of the turbid solution obtained in the step (2.3) to 8-12, and then stirring at 50-80° C. for 24 h;

(2.5) drying the precipitates obtained in the step (2.4) in a certain treatment atmosphere at 25-200° C. for 1-10 h, and then conducting heat treatment at 350-700° C. for 0.5-10 h to obtain the metal hydroxy phosphate, i.e., aromatization catalyst;

The aromatization catalyst is metal hydroxy phosphate $(A_xB_yC_zD_mE_n(OH)_2(PO_4)_6$, $x+y+z+m+n=9$-$10$, $9$-$10 \geq x,y,z,m,n \geq 0)$ and metallic phosphate $(A_xB_yC_zD_mE_n(PO_4)_2$, $x+y+z+m+n=3$, $3 \geq x,y,z,m,n \geq 0)$;

The metals A, B, C, D and E are the same or different and are selected from one or a combination of more than one of Mg, Ca, Sr, Ba, Pb, Cu, Ni, Co, Zn, Zr and Hf;

When the aromatization catalyst contains the transition metals Cu, Ni, Co, Zn, Zr and Hf, the precipitates obtained in the step (2.4) are heat treated at 350-550° C.;

(3) Catalyst pelleting and packing (3.1) respectively tabletting, shaping and screening the dehydrogenation catalyst and the aromatization catalyst prepared in the above steps to the specified particle size;

(3.2) packing the dehydrogenation catalyst and the aromatization catalyst shaped in the step (3.1) in sequence in a single fixed tube, and separating the dehydrogenation catalyst and the aromatization catalyst by quartz wool;

(3.3) reducing the double bed catalyst obtained in the step (3.2) in hydrogen atmosphere at 350-750° C. for 1-5 h.

(4) at reaction temperature of 150-450° C. and reaction pressure of 1-50 atm, introducing ethanol into a reactor packed with the catalysts to produce methylbenzyl alcohol.

In the step (1.1), the solution of transition metal salts is aqueous solution and/or alcohol solution; the concentration of the transition metals aqueous solution is 0.075 g/mL-0.75 g/mL; the concentration of the transition metals alcohol solution is 0.075-0.225 g/mL; soluble salts of transition metals are selected from one or a combination of more than one of chloride, nitrate, diacetone, sulfate and acetate; the alcohol solvent is selected from methanol and/or ethanol.

In the step (1.4), the inert atmosphere is one or a combination of more than one of He, Ar and $N_2$.

In the step (2.5), the treatment atmosphere is one or a combination of more than one of $H_2$, He, Ar, $N_2$ and $O_2$.

In the step (1.4) and the step (3.3), the hydrogen reduction concentration is one of 5-20 vol % $H_2/N_2$, $H_2$/He and $H_2$/Ar.

A catalyst for producing methylbenzyl alcohol from ethanol by catalytic conversion comprises the dehydrogenation catalyst and the aromatization catalyst; the two catalysts are packed in one reactor or respective reactors; and components are measured by weight percent;

(1) dehydrogenation catalyst, is transition metals or oxides thereof; the transition metals are a single or multi-element component; chloride, nitrate, diacetone, sulfate or acetate of the transition metals is adopted as a precursor, and roasted and reduced to obtain metals or oxides thereof, or supported on a support, and loading is 0.01-50 wt % of the weight of the support;

transition metals are selected from one or a combination of more than one of Co, Ni, Cu, Ag, Pd, Rh, Ru, Pt, Ir, Zn and Y.

(2) aromatization catalyst, is metal hydroxy phosphate and/or metal phosphate, metal hydroxy phosphate $A_xB_yC_zD_mE_n(OH)_2(PO_4)_6$, $x+y+z+m+n=9$-$10$, $9$-$10 \geq x,y,z,m,n \geq 0$; metal phosphate $A_xB_yC_zD_mE_n(PO_4)_2$, $x+y+z+m+n=3$, $3 \geq x,y,z,m,n \geq 0$; the phosphate compound is one or a mechanical mixture of more than one.

The metals A, B, C, D and E are the same or different and are selected from one or a combination of more than one of Mg, Ca, Sr, Ba, Pb, Cu, Ni, Co, Zn, Zr and Hf;

In the dehydrogenation catalyst, the transition metal is preferably Cu, a supported catalyst is adopted, and the support is $Al_2O_3$, $SiO_2$, $ZrO_2$, ZnO, MgO, carbon or carbon/oxide compound. The support is preferably carbon, and the loading of Cu is 0.01-50 wt % of that of the carbon support, and preferably 0.1-5 wt %.

The aromatization catalyst is preferably $Ca_xCo_y(OH)_2(PO_4)_6$, $Ca_{10}(OH)_2(PO_4)_6$ or $Sr_{10}(OH)_2(PO_4)_6$;

In addition, an atmospheric fix-bed reactor is preferred. When a single reactor is used, the dehydrogenation catalyst and the aromatization catalyst can have a mechanical mixed single bed or double bed structure. When a plurality of reactors are used, the bed of the dehydrogenation catalyst is in front.

Compared with the current production technology, this invention provides a route and corresponding catalysts for directly producing methylbenzyl alcohols from ethanol from a wide range of sources. The selectivity of methylbenzyl alcohols is up to 72% at reaction temperature of 225° C. Moreover, this innovative reaction route produces hydrogen as co-product, and can be directly used in fuel cells. In addition, the route also produces high carbon number ($C_{4-12}$) alcohols which can be used as fuels or oil additives to partially replace petroleum-based products, thus partly reducing the dependence on petroleum.

DETAILED DESCRIPTION

The present invention is described below in detail through some embodiments. However, the present invention is not limited to these embodiments.

The dehydrogenation catalyst is represented by wMetal/support, wherein w=weight percent of metal loading in total weight of the catalysts x100.

The aromatization catalyst is represented by HAP-M and PO-M, wherein HAP represents hydroxymetallic apatite; PO represents metal phosphate; and M refers to metal and is one or more of Mg, Ca, Sr, Ba, Pb, Cu, Ni, Co, Zn, Zr, Hf, etc.

Embodiment 1

Synthesis of Carbon Supported Cu Catalyst:

(1) carbon support is dried at 120° C. for 2 h to remove physical adsorption water on its surface;

(2) $Cu(NO_3)_2 \cdot 3H_2O$ aqueous solution with a mass concentration of 0.75 g/mL is prepared;

(3) at 25° C., an incipient wetness impregnation method is used to treat the solution in the step (2) on carbon to stand for 0.1 h;

(4) the obtained mixture after staying for 0.1 h at room temperature is then dried at 50° C. for 0.5 h to obtain corresponding catalyst precursors;

(5) the precursor obtained in the step (4) is dried at 140° C. for 0.5 h, treated in inert atmosphere at 350° C. for 1 h, and then treated in hydrogen atmosphere at 450° C. for 2 h to obtain carbon supported Cu catalyst, which is denoted as 10Cu/carbon (entry 1 in Table 1).

Figure 1:
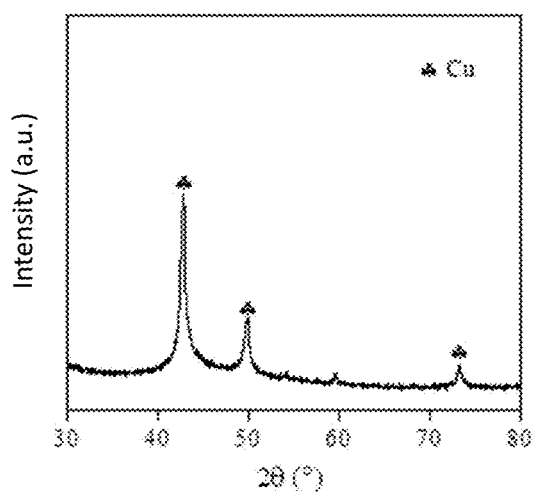
FIG. 1 is an XRD spectrum of 10Cu/carbon catalyst in embodiment 1.

The XRD spectrum of 10Cu/carbon catalyst is shown in FIG. 1.

TABLE 1

Corresponding Relationship between Sample Number and Preparation Conditions in Embodiment 1

| Entry | Catalyst | Loading/wt % | Support | Metals | Solvent | Metal Concentration/g/mL | Reduction Temperature/° C. |
|---|---|---|---|---|---|---|---|
| 1 | 10u/Carbon | 10 | Carbon | Copper nitrate | Water | 0.75 | 450 |
| 2 | 10Cu/SiO$_2$ | 10 | SiO$_2$ | Copper nitrate | Water | 0.75 | 450 |
| 3 | 10Cu/Al$_2$O$_3$ | 10 | Al$_2$O$_3$ | Copper nitrate | Water | 0.75 | 450 |
| 4 | 10Cu/ZrO$_2$ | 10 | ZrO$_2$ | Copper nitrate | Water | 0.75 | 450 |
| 5 | 10Cu/ZnO | 10 | ZnO | Copper nitrate | Water | 0.75 | 450 |
| 6 | 10Cu/MgO | 10 | MgO | Copper nitrate | Water | 0.75 | 450 |
| 7 | 10Cu/C/SiO$_2$ | 10 | C/SiO$_2$ | Copper nitrate | Water | 0.75 | 450 |
| 8 | 5Cu/carbon | 5 | Carbon | Copper nitrate | Water | 0.4 | 450 |
| 9 | 10Ni/carbon | 10 | Carbon | Nickel nitrate | Water | 0.8 | 600 |

Embodiment 2

Synthesis of SiO$_2$ Supported Cu Catalyst:

(1) SiO$_2$ support is dried at 120° C. for 2 h to remove physical adsorption water on its surface;

(2) Cu(NO$_3$)$_2$·3H$_2$O aqueous solution with a mass concentration of 0.75 g/mL is prepared;

(3) at 25° C., an incipient wetness impregnation method is used to treat the solution in the step (2) on SiO$_2$ to stand for 2 h;

(4) the obtained mixture after staying for 2 h at room temperature is then dried at 50° C. for 8 h to obtain corresponding catalyst precursors;

(5) the precursor obtained in the step (4) is treated in hydrogen atmosphere at 450° C. for 2 h to obtain SiO$_2$ supported Cu catalyst, which is denoted as 10Cu/SiO$_2$ (entry 2 in Table 1).

Figure 2:
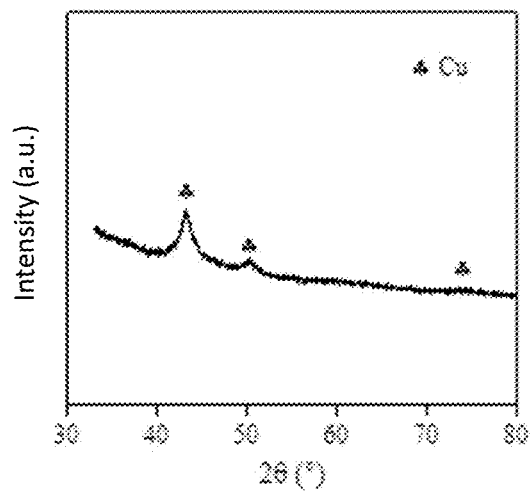
FIG. 2 is an XRD spectrum of 10Cu/$SiO_2$ catalyst in embodiment 2.

The XRD spectrum of 10Cu/SiO$_2$ catalyst is shown in FIG. 2.

The preparation conditions of other oxide supported metal catalysts are the same as those in embodiment 2. The corresponding relationship between the sample number and the preparation conditions are shown in Table 1.

Embodiment 3

Synthesis of Metal Hydroxy Phosphate Ca$_8$Co$_2$(OH)$_2$(PO$_4$)$_6$:

(1) calcium nitrate and cobalt nitrate are dissolved in water to prepare aqueous solution with a total mole fraction of 0.6 M;

(2) diammonium phosphate is dissolved in water to prepare aqueous solution with a mole fraction of 0.4 M, wherein the molar ratio of Ca+Co to P is 1.67;

(3) the calcium nitrate and cobalt nitrate solution prepared in the step (1) is added in the aqueous solution prepared in the step (2) dropwise (10 mL/min), and fully stirred for 60 min;

(4) stronger ammonia water (~25 wt %) is added to the turbid solution obtained in the step (3) to adjust the pH value of the whole system to above 11, and then stirred at 80° C. for 24 h;

(5) pink precipitates obtained in the step (4) are dried in specific atmosphere at 50° C. for 10 h, and then roasted at 550° C. for 2 h to obtain Ca$_8$Co$_2$(OH)$_2$(PO$_4$)$_6$.

The atomic ratios of Ca and Co can be adjusted by controlling the mass ratio of added calcium nitrate to added cobalt nitrate, and the preparation method is the same as that in embodiment 3. The corresponding relationship between the sample number and the preparation conditions are shown in Table 2.

The species and ratio of metal atoms can be adjusted by controlling the added nitrate, and the preparation method is the same as that in embodiment 3. The corresponding relationship between the sample number and the preparation conditions are shown in Table 2.

TABLE 2

Corresponding Relationships between Sample Number and Preparation Conditions in Embodiment 3

| Entry | Catalyst | Metals | Reduction/Treatment Temperature/° C. |
|---|---|---|---|
| 1 | HAP-8Ca2Co | Calcium nitrate and cobalt nitrate | 550 |
| 2 | HAP-5Ca5Co | Calcium nitrate and cobalt nitrate | 550 |
| 3 | HAP-Ca | Calcium nitrate | 600 |
| 4 | HAP-Sr | Strontium nitrate | 600 |
| 5 | HAP-Mg | Magnesium nitrate | 600 |
| 6 | HAP-Ba | Barium nitrate | 600 |
| 7 | PO-2Ca1Co | Calcium nitrate and cobalt nitrate | 550 |
| 8 | PO-Ca | Calcium nitrate | 600 |
| 9 | PO-Mg | Magnesium nitrate | 600 |

Embodiment 4

Synthesis of Metal Calcium Phosphate Ca$_2$Co(PO$_4$)$_2$:

(1) calcium hydroxide and cobalt hydroxide (Ca$^{2+}$/Co$^{2+}$=2:1, molar ratio) are dispersed in water to prepare corresponding solid suspension liquid, and stirred;

(2) 10 wt % of H$_3$PO$_4$ solution is prepared;

(3) The phosphoric acid solution prepared in the step (2) is added in the solid suspension liquid prepared in the step (1) and fully stirred, the amount of the phosphoric acid added is controlled by the pH value of the suspended solids, and then intense stirring is conducted for 3 h;

(4) While precipitates obtained in the step (3) are dried in specific atmosphere at 25-200° C. for 2 h, and then roasted at 600° C. for 2 h to obtain Ca$_2$Co(PO$_4$)$_2$.

The atomic ratios of Ca and Co can be adjusted by controlling the mass ratio of added calcium nitrate to added cobalt nitrate, and the preparation method is the same as that in embodiment 4. The corresponding relationship between the sample number and the preparation conditions are shown in Table 2.

The species and ratio of metal atoms can be adjusted by controlling the added nitrate, and the preparation method is the same as that in embodiment 4. The corresponding relationship between the sample number and the preparation conditions are shown in Table 2.

Embodiment 5

Catalytic Activity of Dehydrogenation and Aromatization Composite Catalysts of the Single-Reactor and Double-Bed Structure from Ethanol to Methylbenzyl Alcohol Ethanol upgrading is studied in a fix-bed, atmosphere pressure reactor by feeding ethanol as reactant. Reaction conditions are as follows: the catalyst is first packed in the fix-bed reactor with an inner diameter of 8 mm and kept at 225° C. Then, ethanol liquid is fed in a rate of 0.3 mL/h After steady, ethanol conversion and products distribution are analyzed by an on-line gas chromatography (GC). The corresponding relationship between sample number and ethanol upgrading activity is shown in Table 3.

TABLE 3

Corresponding Relationships between Sample Number and Ethanol Conversion and Methylbenzyl Alcohol Selectivity in Embodiment 5

| Entry | Catalyst | Conversion/% | Selectivity/% |
|---|---|---|---|
| 1 | 10Cu/carbon//HAP-8Ca$_2$Co | 16.1 | 72.5 |
| 2 | 10Cu/SiO$_2$//HAP-8Ca2Co | 15.5 | 73.1 |
| 3 | 10Cu/Al$_2$O$_3$//HAP-8Ca2Co | 19.0 | 40.5 |
| 4 | 10Cu/ZrO$_2$//HAP-8Ca2Co | 20.1 | 45.0 |
| 5 | 10Cu/ZnO//HAP-8Ca2Co | 16.5 | 72.1 |
| 6 | 10Cu/MgO//HAP-8Ca2Co | 16.2 | 71.2 |
| 7 | 10Cu/C/SiO$_2$//HAP-8Ca2Co | 17.6 | 70.1 |
| 8 | 5Cu/carbon//HAP-8Ca$_2$Co | 15.9 | 71.1 |
| 9 | 10Ni/carbon//HAP-8Ca$_2$Co | 15 | 65.6 |
| 10 | 10Cu/carbon//HAP-5Ca$_5$Co | 17.6 | 72.8 |
| 11 | 10Cu/carbon//HAP-Ca | 15.5 | 60.1 |
| 12 | 10Cu/carbon//HAP-Sr | 14.9 | 61.0 |
| 13 | 10Cu/carbon//HAP-Mg | 17.1 | 59.5 |
| 14 | 10Cu/carbon//HAP-Ba | 13.5 | 54.9 |
| 15 | 10Cu/carbon//PO-2Ca$_1$Co | 15.9 | 32.5 |
| 16 | 10Cu/carbon//PO-Ca | 16.0 | 36.2 |
| 17 | 10Cu/ carbon//PO-Mg | 16.2 | 30.1 |

Embodiment 6

Effect of Mixing Manners of Dehydrogenation and Aromatization Composite Catalysts on Selectivity of Methylbenzyl Alcohol Ethanol upgrading is studied in a fix-bed, atmosphere pressure reactor by feeding ethanol as reactant, the dehydrogenation catalyst is 10Cu/carbon, and the aromatization catalyst is HAP-8Ca$_2$Co. Reaction conditions are as follows: at atmosphere pressure and reaction temperature of 225° C., ethanol liquid is fed in a rate of 0.3 mL/h, and WHSV= 1.0 h$^{-1}$. Three catalyst mixing manners are used: single reactor and single bed (1), single reactor and double beds (2) and double beds (3). After steady, ethanol conversion and products distribution are analyzed by an on-line gas chromatography (GC). Reaction results are shown in Table 4.

Figure 3:
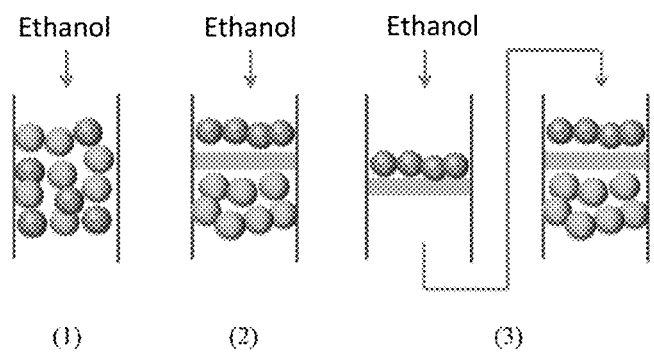
FIG. 3 shows different catalyst mixing manners in embodiment 6.

The catalyst mixing manners are shown in FIG. 3.

TABLE 4

Study of Effect of Dehydrogenation and Aromatization Composite Catalyst Mixing Manner on Methylbenzyl Alcohol Selectivity in Embodiment 6

| Mixing Manner | Conversion/% | Selectivity/% |
|---|---|---|
| (1) | 14.5 | 25.1 |
| (2) | 16.1 | 72.5 |
| (3) | 17.5 | 71.8 |

Embodiment 7

Product Distribution of Ethanol with Different Concentrations by Catalytic Conversion of Dehydrogenation and Aromatization Composite Catalysts of Single-Reactor and Double-Bed Structure Ethanol upgrading is studied in a fix-bed, atmosphere pressure reactor by feeding ethanol as reactant, the dehydrogenation catalyst is 10Cu/carbon, and the aromatization catalyst is HAP-8Ca$_2$Co. Reaction conditions are as follows: the catalyst is first packed in the fix-bed reactor with an inner diameter of 8 mm and kept at 225° C. Then, ethanol liquid is fed in a rate of 0.3 mL/h, and WHSV=1.0 h$^{-1}$. After steady, ethanol conversion and products distribution are analyzed by an on-line gas chromatography (GC). Reaction results are shown in Table 5.

TABLE 5

Study of Effect of Ethanol Concentration on Methylbenzyl Alcohol Selectivity in Embodiment 7

| Feeding (mL/h) | Conversion/% | Selectivity/% |
|---|---|---|
| 0.05 | 34.8 | 50.1 |
| 0.1 | 27.5 | 58.9 |
| 0.15 | 21.0 | 62.3 |
| 0.2 | 18.6 | 67.1 |
| 0.27 | 16.1 | 72.5 |
| 0.32 | 13.4 | 72.1 |
| 2.7 | 2.2 | 28.9 |

Embodiment 8

Product Distribution of Ethanol by Catalytic Conversion of Dehydrogenation and Aromatization Composite Catalysts of Single-Reactor and Double-Bed Structure at Different Temperatures Ethanol upgrading is studied in a fix-bed, atmosphere pressure reactor by feeding ethanol as reactant, the dehydrogenation catalyst is 10Cu/carbon, and the aromatization catalyst is HAP-8Ca$_2$Co. Reaction conditions are as follows: the catalyst is first packed in the fix-bed reactor with an inner diameter of 8 mm and kept at different reaction temperature (100-450° C.). Then, ethanol liquid is fed in a rate of 0.3 mL/h, and WHSV=1.0 h$^{-1}$. After steady, ethanol conversion and products distribution are analyzed by an on-line gas chromatography (GC). Reaction results are shown in Table 6.

Figure 4:
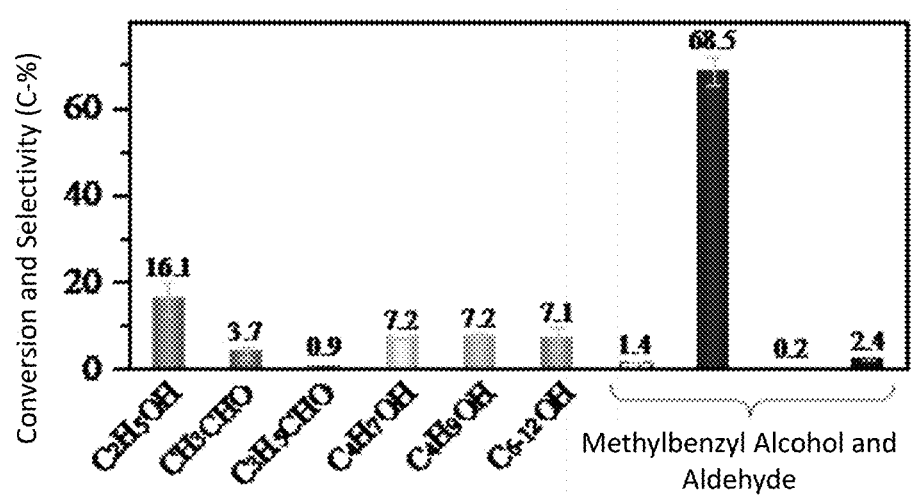
FIG. 4 is data of specific product distributions at reaction temperature of 225° C. in embodiment 8.

The product distribution at reaction temperature of 225° C. is shown in FIG. 4.

TABLE 6

Product Distribution of Ethanol by catalytic conversion at Different Temperatures in Embodiment 8

| Temperature | Conversion/% | Selectivity/% |
|---|---|---|
| 150 | 1.2 | 42.7 |
| 175 | 3.9 | 61.1 |
| 200 | 8.9 | 68.3 |
| 225 | 16.1 | 72.5 |
| 250 | 20.4 | 67.2 |
| 275 | 28.7 | 65.0 |
| 300 | 37.7 | 65.3 |
| 325 | 36.7 | 54.0 |
| 350 | 45.8 | 43.1 |
| 400 | 75.1 | 22.0 |

The invention claimed is:

1. A method for producing methylbenzyl alcohol from ethanol by catalytic conversion, comprising the following steps:
   (1) production of dehydrogenation catalyst, comprising
   (1.1) preparing an aqueous solution of transition metal salts and/or and an alcohol solution of the transition metal salts;
   wherein a concentration of the aqueous solution of the transition metal salts is 0.075 g/mL-0.75 g/mL; a concentration of the alcohol solution of the transition metal salts is 0.075-0.225 g/mL; the transition metal salts are selected from one or a combination of more than one of chloride, nitrate, diacetone, sulfate and acetate; alcohol solvent is methanol and/or ethanol,
   (1.2) using an incipient wetness impregnation method to impregnate a support for 1-3 times using the aqueous solution or the alcohol solution of the transition metal salts prepared in the step (1.1); after impregnation, staying obtained mixture at room temperature for 0.1-2 h;
   (1.3) placing the obtained mixture from the step (1.2) into a 50° C. oven for drying for 0.1-20 h;
   (1.4) drying the dried product in the step (1.3) at 100-150° C. for 0.5-2 h, and treating a dehydrogenation catalyst precursor in an inert atmosphere and a hydrogen atmosphere in sequence or in the hydrogen atmosphere directly to obtain supported transition metal catalyst, which is the dehydrogenation catalyst, recorded as transition metal/support;
   wherein the transition metal is selected from one or a combination of more than one of Co, Ni, Cu, Ag, Pd, Rh, Ru, Pt, Ir, Zn and Y;
   the support is selected from carbon, $Al_2O_3$, $SiO_2$, $ZrO_2$, ZnO and MgO; if the support is carbon, the dehydrogenation catalyst precursor is treated in the inert atmosphere at 350-450° C. for 1-5 h, and then reduced in the hydrogen atmosphere at 350-600° C. for 0.5-5 h;
   if the support is $Al_2O_3$, $SiO_2$, $ZrO_2$, ZnO or MgO, the dehydrogenation catalyst precursor is reduced directly in the hydrogen atmosphere at 350-600° C. for 2-5 h;
   (2) production of aromatization catalyst, comprising:
   (2.1) dissolving nitrates of metals A, B, C, D and E in water to prepare corresponding aqueous solutions;
   (2.2) dissolving diammonium phosphate in water to prepare the corresponding aqueous solution;
   (2.3) adding the nitrate solutions prepared in the step (2.1) in the aqueous solution prepared in the step (2.2) dropwise, and fully stirring; wherein a molar ratio of metals to phosphorus is 1.5-1.67;
   (2.4) using ammonia water to adjust the pH value of the turbid solution obtained in the step (2.3) to 8-12, and then stirring at 50-80° C. for 24 h;
   (2.5) drying the precipitates obtained in the step (2.4) in a treatment atmosphere at 25-200° C. for 1-10 h, and then conducting heat treatment at 350-700° C. for 0.5-10 h to obtain metal hydroxy phosphate, which is the aromatization catalyst;
   the aromatization catalyst is metal hydroxy phosphate $(A_xB_yC_zD_mE_n(OH)_2(PO_4)_6$, x+y+z+m+n=9-10, 9-10≥x,y,z,m,n≥0) and metallic phosphate $(A_xB_yC_zD_mE_n(PO_4)_2$, x+y+z+m+n=3, 3≥x,y,z,m,n≥0);
   wherein the metals A, B, C, D and E are the same or different and are selected from one or a combination of more than one of Mg, Ca, Sr, Ba, Pb, Cu, Ni, Co, Zn, Zr and Hf;
   when the aromatization catalyst contains the transition metal Cu, Ni, Co, Zn, Zr and Hf, the precipitates obtained in the step (2.4) are heat treated at 350-550° C.;
   (3) pelleting and packing the dehydrogenation catalyst and the aromatization catalyst, comprising:
   (3.1) respectively tabletting, shaping and screening the dehydrogenation catalyst and the aromatization catalyst prepared in the above steps to a specified particle size;
   (3.2) packing the dehydrogenation catalyst and the aromatization catalyst shaped in the step (3.1) in sequence in a single fixed tube, and separating the dehydrogenation catalyst and the aromatization catalyst by quartz wool;
   (3.3) reducing a double bed catalyst obtained in the step (3.2) in hydrogen atmosphere at 350-750° C. for 1-5 h; and
   (4) at reaction temperature of 150-450° C. and reaction pressure of 1-50 atm, introducing ethanol into a reactor packed with the double bed catalyst to produce methylbenzyl alcohol.

2. The method according to claim 1, wherein in the step (1.4), the inert atmosphere is one or a combination of more than one of He, Ar and $N_2$.

3. The method according to claim 2, wherein in the step (2.5), the treatment atmosphere is one or a combination of more than one of Hz, He, Ar, $N_2$ and $O_2$.

4. The method according to claim 1, wherein in the step (1.4) and the step (3.3), the hydrogen reduction concentration is one of 5-20 vol % $H_2/N_2$, $H_2$/He and $H_2$/Ar.

5. The method according to claim 2, wherein in the step (1.4) and the step (3.3), the hydrogen reduction concentration is one of 5-20 vol % $H_2/N_2$, $H_2$/He and $H_2$/Ar.

* * * * *